(12) United States Patent
Perez-Soler et al.

(10) Patent No.: US 8,283,382 B2
(45) Date of Patent: Oct. 9, 2012

(54) VITAMIN K FOR PREVENTION AND TREATMENT OF SKIN RASH SECONDARY TO ANTI-EGFR THERAPY

(75) Inventors: Roman Perez-Soler, New York, NY (US); Yi-He Ling, Briarwood, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 143 days.

(21) Appl. No.: 12/788,015

(22) Filed: May 26, 2010

(65) Prior Publication Data

US 2010/0324148 A1 Dec. 23, 2010

Related U.S. Application Data

(62) Division of application No. 11/886,803, filed as application No. PCT/US2006/014158 on Apr. 12, 2006, now Pat. No. 7,745,494.

(60) Provisional application No. 60/671,563, filed on Apr. 15, 2005.

(51) Int. Cl.
*A61K 31/12* (2006.01)
(52) U.S. Cl. ...................................... 514/682
(58) Field of Classification Search .................. None
See application file for complete search history.

(56) References Cited

U.S. PATENT DOCUMENTS

| | | |
|---|---|---|
| 4,294,852 A | 10/1981 | Wildnauer et al. |
| 4,374,775 A | 2/1983 | Dotz et al. |
| 4,719,239 A | 1/1988 | Muller et al. |
| 4,840,970 A | 6/1989 | Ohasi et al. |
| 4,906,411 A | 3/1990 | Shinnaka et al. |
| 4,966,779 A | 10/1990 | Kirk |
| 5,134,127 A | 7/1992 | Stella et al. |
| 5,155,031 A | 10/1992 | Posner et al. |
| 5,180,747 A | 1/1993 | Matsuda et al. |
| 5,356,636 A | 10/1994 | Schneider et al. |
| 5,376,645 A | 12/1994 | Stella et al. |
| 5,412,125 A | 5/1995 | Philippe et al. |
| 5,510,391 A | 4/1996 | Elson |
| 5,637,741 A | 6/1997 | Matsumoto et al. |
| 5,643,583 A | 7/1997 | Voultoury et al. |
| 5,650,156 A | 7/1997 | Grinstaff et al. |
| 5,770,774 A | 6/1998 | Joo et al. |

(Continued)

FOREIGN PATENT DOCUMENTS

DE 3514724 A1 10/1986

(Continued)

OTHER PUBLICATIONS

Abdelmohsen, Kotb et al., "Epidermal Growth Factor Receptor Is a Common Mediator of Quinone-induced Signaling Leading to Phosphorylation of Connexin-43," The Journal of Biological Chemistry, vol. 278(40):38360-38367 (2003).

(Continued)

*Primary Examiner* — Craig Ricci
(74) *Attorney, Agent, or Firm* — Nelson Mullins Riley & Scarborough LLP; Jane E. Remillard, Esq.; Cynthia L. Kanik (57) ABSTRACT

The invention provides methods and compositions for treating and preventing a skin rash secondary to anti-epidermal growth factor receptor (EGFR) therapy, where the method comprises applying a vitamin K analog or a phosphatase inhibitor to the skin.

10 Claims, 7 Drawing Sheets

U.S. PATENT DOCUMENTS

| | | | |
|---|---|---|---|
| 5,785,976 | A | 7/1998 | Westesen et al. |
| 5,885,486 | A | 3/1999 | Westesen et al. |
| 5,916,749 | A | 6/1999 | Bandman et al. |
| 6,013,665 | A | 1/2000 | DeMichele et al. |
| 6,110,891 | A | 8/2000 | Pusztai et al. |
| 6,160,007 | A | 12/2000 | DeMichele et al. |
| 6,187,822 | B1 | 2/2001 | Leibovich |
| 6,207,176 | B1 | 3/2001 | Howard et al. |
| 6,264,986 | B1 | 7/2001 | Hahnlein et al. |
| 6,383,471 | B1 | 5/2002 | Chen et al. |
| 6,426,078 | B1 | 7/2002 | Bauer et al. |
| 6,428,949 | B1 | 8/2002 | Bandman et al. |
| 6,524,594 | B1 | 2/2003 | Santora et al. |
| 6,537,579 | B1 | 3/2003 | Desai et al. |
| 6,576,660 | B1 | 6/2003 | Liao et al. |
| 6,579,994 | B2 | 6/2003 | Sankarasubbier et al. |
| 6,582,710 | B2 | 6/2003 | Deckers et al. |
| 6,596,287 | B2 | 7/2003 | Deckers et al. |
| 6,599,513 | B2 | 7/2003 | Deckers et al. |
| 6,660,306 | B2 | 12/2003 | Peshoff |
| 6,696,484 | B2 | 2/2004 | Liao et al. |
| 6,774,100 | B2 | 8/2004 | Vishnupad |
| 6,780,439 | B2 | 8/2004 | Wilk |
| 6,979,454 | B1 | 12/2005 | Lindahl et al. |
| 7,094,431 | B2 | 8/2006 | Peshoff |
| 7,252,816 | B1 | 8/2007 | Angel et al. |
| 7,326,690 | B2 | 2/2008 | Henry et al. |
| 7,402,557 | B2 | 7/2008 | Miller et al. |
| 7,405,188 | B2 | 7/2008 | Chen |
| 2002/0061304 | A1 | 5/2002 | Miller et al. |
| 2003/0139353 | A1 | 7/2003 | Jackson et al. |
| 2003/0158165 | A1 | 8/2003 | Wilk |
| 2003/0170187 | A1 | 9/2003 | Marchal |
| 2004/0040011 | A1 | 2/2004 | Bosworth et al. |
| 2004/0047852 | A1 | 3/2004 | Kennedy |
| 2004/0062817 | A1 | 4/2004 | Peshoff |
| 2004/0081674 | A1 | 4/2004 | Franke |
| 2004/0138218 | A1 | 7/2004 | Pallen et al. |
| 2004/0265396 | A1 | 12/2004 | Peshoff |
| 2005/0048008 | A1 | 3/2005 | Gupta |
| 2005/0092969 | A1 | 5/2005 | Ueda et al. |
| 2005/0118187 | A1 | 6/2005 | Yu |
| 2005/0148521 | A1 | 7/2005 | Ben-Sasson et al. |
| 2006/0002439 | A1 | 1/2006 | Lee |
| 2006/0058398 | A1 | 3/2006 | Kamei et al. |
| 2006/0216342 | A1 | 9/2006 | Torchilin et al. |
| 2006/0275504 | A1 | 12/2006 | Chen |
| 2007/0025950 | A1 | 2/2007 | Elson |
| 2007/0142462 | A1 | 6/2007 | Kennedy |
| 2007/0238697 | A1 | 10/2007 | Jackson et al. |

FOREIGN PATENT DOCUMENTS

| | | |
|---|---|---|
| DE | 10003786 A1 | 8/2001 |
| EP | 0392845 A2 | 10/1990 |
| EP | 1214930 B1 | 6/2002 |
| JP | 2002-517436 | 6/2002 |
| JP | 2004-500392 | 1/2004 |
| JP | 2005-20651 | 1/2005 |
| JP | 2005-206521 | 8/2005 |
| WO | 94/23023 A1 | 10/1994 |
| WO | 97/39746 A1 | 10/1997 |
| WO | 99/63982 A1 | 12/1999 |
| WO | 01/64214 A2 | 9/2001 |
| WO | 01/67896 A2 | 9/2001 |
| WO | 01/91740 A2 | 12/2001 |
| WO | 02/13780 A1 | 2/2002 |
| WO | 02/20525 A2 | 3/2002 |
| WO | 02/47642 A1 | 6/2002 |
| WO | 03/018033 A1 | 3/2003 |
| WO | 03/061566 A2 | 7/2003 |
| WO | 03/101415 A1 | 12/2003 |
| WO | 2004/019923 A1 | 3/2004 |
| WO | 2005/032523 A1 | 4/2005 |
| WO | 2006/029893 A2 | 3/2006 |
| WO | 2006/056889 A2 | 6/2006 |
| WO | 2006/107827 A1 | 10/2006 |
| WO | 2006/113479 A2 | 10/2006 |
| WO | 2007/147128 A2 | 12/2007 |
| WO | 2008/004231 A1 | 1/2008 |

OTHER PUBLICATIONS

Baselga, J. et al., "Phase I Safety, Pharmacokinetic, and Pharmacodynamic Trial of ZD1839, a Selective Oral Epidermal Growth Factor Receptor Tyrosine Kinase Inhibitor, in Patients With Five Selected Solid Tumor Types," Journal of Clinical Oncology, vol. 20(21):4292-4302 (2002).

Bae, Eun Young et al., "A New VHR Dual-Specificity Protein Tyrosine Phosphatase Inhibitor from Dendrobium moniliforme," Planta Med., vol. 70:869-870 (2004).

Bernier, J. et al., "Consensus guidelines for the management of radiation dermatitis and coexisting acne-like rash in patients receiving radiotherapy plus EGFR inhibitors for the treatment of squamous cell carcinoma of the head and neck," Annals of Oncology, vol. 19(1):142-149 (2007).

Busam, K.J. et al., "Cutaneous side-effects in cancer patients treated with the antiepidermal growth factor receptor antibody C225," British Journal of Dermatology, vol. 144:1169-1176 (2001).

Clark, G.M. et al., "Rash severity is predictive of increased survival with erlotinib HCl," Proceedings of the American Society of Clinical Oncology, vol. 22, Abstr. No. 786 (2003).

Cohen, Ezra E.W. et al., "Phase II Trial of ZD1839 in Recurrent or Metastatic Squamous Cell Carcinoma of the Head and Neck," Journal of Clinical Oncology, vol. 21(10):1980-1987 (2003).

deBeer, Edwin J. et al., "Routes of Administration of Materials Capable of Acting as Vitamin K," Proc. Soc. Exp. Biol and Med., vol. 46:535-537 (1941).

Elson, Melvin L., "Topical Phytonadione (Vitamin K1) in the Treatment of Actinic and Traumatic Purpura," Cosmetic Dermatology, vol. 8(12):25-27 (1995).

Gerling, Norbert et al., "The tyrosine phosphatase inhibitor orthovanadate mimics NGF-induced neuroprotective signaling in rat hippocampal neurons," Neurochemistry International, vol. 44:505-520 (2004).

Guo, Jian-Hwa, "Excipient Update," Carbopol Polymers for Pharmaceutical Drug Delivery Applications, vol. 6 (2003).

Lage, Augustin et al., "Targeting epidermal growth factor receptor signaling: early results and future trends in oncology," Annals of Medicine, vol. 35(5):327-336 (2003).

Lee, Kyeong et al., "CD45 Protein-Tyrosine Phosphatase Inhibitor Development," Current Topics in Medicinal Chemistry, vol. 3:797-807 (2003).

Liem, David A. et al., "The Tyrosine Phosphatase Inhibitor Bis(Maltolato)-Oxovanadium Attenuates Myocardial Reperfusion Injury by Opening ATP-Sensitive Potassium Channels," The Journal of Pharmacology and Experimental Therapeutics, vol. 309(3):1256-1262 (2004).

LoRusso, Patricia M., "Phase I Studies of ZD1839 in Patients With Common Solid Tumors," Seminars in Oncology, vol. 30(1, Suppl. 1):21-29 (2003).

Lou, Wendy W. et al., "Effects of Topical Vitamin K and Retinol on Laser-Induced Purpura on Nonlesional Skin," Dermatol. Surg., vol. 25:942-944 (1999).

Matschiner, John T. et al., "Metabolism and Vitamin K Activity of cis Phylloquinone in Rats," J. Nutrition, vol. 102:625-630 (1972).

Page, R.C. et al., "Dermatitis from Topical Application of 2-Methyl-1:4-Naphthoqunone (Synthetic Vitamin K Analogue)," The American Journal of the Medical Sciences, vol. 203:566-569 (1942).

Perea, Sofia et al., "Predictors of Sensitivity and Resistance to Epidermal Growth Factor Receptor Inhibitors," Clinical Lung Cancer, vol. 6(Suppl. 1):S30-S34 (2004).

Perez-Soler, Roman et al., "HER1/EGFR Inhibitor-Associated Rash: Future Directions for Management and Investigation Outcomes from the HER1/EGFR Inhibitor Rash Management Forum," The Oncologist, vol. 10:345-356 (2005).

Perez-Soler, R. et al., "Topical vitamin K3 (Vit K3, Menadione) prevents erlotinib and cetuximab-induced EGFR inhibition in the skin," Journal of Clinical Oncology, vol. 18S(Suppl.):3036 (2006).

Rodeck, Ulrich et al., "EGF-R dependent regulation of keratinocyte survival," Journal of Cell Science, vol. 110:113-121 (1997).

Russell, H.K. et al., "Effect of Topical Application of 2-Methyl-1,4-Naph-Thoquinone (Synthetic Vitamin K Analogue) on the Prothrombin Level of Newborn Infants. With Reference to a Simplified Micro-prothrombin Test," Am. J. Med. Sci., vol. 202:355-359 (1941).

Sah, Peter P.T., "Synthesis of 3-Methyl-4-Amino-1-naphthol hydrochloride (vitamin K) and related vitamin-K-active compounds," Zeitschrift fuer Vitamin-, Hormon- und Fermentforschung, vol. 3(3-4):324-345 (1949-1950).

Saltz, L. et al., "The presence and intensity of the cetuximab-induced acne-like rash predicts increased survival in studies across multiple malignancies," Proceedings of the American Society of Clinical Oncology, vol. 22, Abstr. No. 817 (2003).

Shah, Neha S. et al., "The effects of topical vitamin K on bruising after laser treatment," J. Am. Acad. Dermatol., vol. 47:241-244 (2002).

Smolinske, Susan C., "Benzyl Alcohol," Handbook of Food, Drug, and Cosmetic Excipients, p. 47 (1992).

Sorg, Olivier et al., "Oxidative Stress-Independent Depletion of Epidermal Vitamin A by UVA," J. Invest. Dermatol., vol. 118:513-518 (2002).

Soulieres, Denis et al., "Multicenter Phase II Study of Erlotinib, an Oral Epidermal Growth Factor Receptor Tyrosine Kinase Inhibitor, in Patients With Recurrent or Metastatic Squamous Cell Cancer of the Head and Neck," Journal of Clinical Oncology, vol. 22(1):77-85 (2004).

Susman, Ed, "Rash correlates with tumour response after cetuximab," The Lancet, Oncology, vol. 5:647 (2004).

Swarbrick, James et al., Encyclopedia of Pharmaceutical Technology, Second Edition, vol. 1, p. 2 (2002).

Ulbrich, A.P., "Topical application of menadione, a synthetic vitamin K: Preliminary report," J. Am. Osteopathic Assoc., vol. 60:370-374 (1961).

U.S. Department of Health and Human Services, "Guidance for Industry, Container Closure Sytems for Packaging Human Drugs and Biologics, Chemistry, Manufacturing, and Controls Documentation," (1999).

Vanhoefer, Udo et al., "Phase I Study of the Humanized Antiepidermal Growth Factor Receptor Monoclonal Antibody EMD72000 in Patients With Advanced Solid Tumors That Express the Epidermal Growth Factor Receptor," J. Clin. Oncol., vol. 22:175-184 (2004).

International Search Report for Application No. PCT/US06/14158, dated Feb. 16, 2007.

International Preliminary Report on Patentability for Application No. PCT/US2006/014158, dated Oct. 16, 2007.

Adachi, T. et al., "PP1390 Mechanism of antitumor action of Menadione (Vitamine K3)," Nihon Gekagakkai Zasshi (J. Japan Surgical Soc.) vol. 103, Special Issue, p. 654 (2002).

Jacot, W. et al., "Acneiform eruption induced by epidermal growth factor receptor inhibitors in patients with solid tumours," British Journal of Dermatology, vol. 151:232-257 (2004).

Lacouture, Mario E., "Insights Into the Pathophysiology and Management of Dermatologic Toxicities to EGFR-Targeted Therapies in Colorectal Cancer," Cancer Nursing, vol. 30(4S):S17-S26 (2007).

Nannery, Lillian B. et al., "Immunolocalization of Epidermal Growth Factor Receptors in Normal Developing Human Skin," J. Invest. Dermatol., vol. 94:742-748 (1990).

Osada, Shinji et al., "New Approach to Cancer Therapy: The Application of Signal Transduction to Anti-Cancer Drug," Curr. Med. Chem., vol. 3:119-131 (2003).

Perez-Soler, R., "Can rash associated with HER1/EGFR inhibition be used as a marker of treatment outcome?" Oncology, vol. 17(11 Suppl. 12):23-28 (2003).

Potthoff, K. et al., "Interdisciplinary management of EGFR-inhibitor-induced skin reactions: a German expert opinion," Annals of Oncology, vol. 22:524-535 (2011).

Saltz, Leonard B. et al., "Phase II Trial of Cetuximab in Patients With Refractory Colorectal Cancer That Expresses the Epidermal Growth Factor Receptor," J. Clin. Oncol., vol. 22:1201-1208 (2004).

Satoh, Yachiyo et al., "Drug eruption due to gefitinib (IRESSA)," Rinsho Hifuka (Clinical Dermatology) vol. 58 (5):28-32 (2004).

Van Doorn, R. et al., "Follicular and epidermal alterations in patients treated with ZD1839 (Iressa), an inhibitor of the epidermal growth factor receptor," British Journal of Dermatology, vol. 147:598-601 (2002).

European Summons to Attend Oral Proceedings for Application No. 06750246.8, 6 pages, dated Apr. 4, 2012.

Japanese Office Action for Application No. JP2008-506765, 15 pages, dated Mar. 6, 2012.

European Office Action for Application No. 10195772.8, 8 pages, dated Nov. 15, 2011.

VITAMIN K FOR PREVENTION AND TREATMENT OF SKIN RASH SECONDARY TO ANTI-EGFR THERAPY

CROSS-REFERENCE TO RELATED APPLICATION

This application is a divisional of U.S. application Ser. No. 11/886,803, filed on Jan. 9, 2009, which is a National Stage entry of PCT/US2006/014158, filed on Apr. 12, 2006, which claims the benefit of U.S. Provisional Application No. 60/671,563, filed on Apr. 15, 2005, the entire contents of each of these applications is hereby incorporated herein by reference.

STATEMENT OF GOVERNMENT SUPPORT

The invention disclosed herein was made with U.S. Government support under National Institutes of Health grant numbers CA 84119 and 91784. Accordingly, the U.S. Government has certain rights in this invention.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

The epidermal growth factor receptor (EGFR) is a transmembrane protein expressed in all epithelial surfaces. It plays an important physiological role in epithelial repair and regeneration. Epidermal growth factor (EGF) is a peptide secreted by salivary glands and other glands associated with epithelial surfaces that binds to a specific area in the extracellular domain of EGFR. Upon binding it generates a signal that is transmitted inside the cell. The first intracellular event as a result of EGF binding is a conformational change of the intracellular domain of EGFR that allows adenosine 5'-triphosphate (ATP) to enter the so-called tyrosine kinase (TK) domain, a pocket that contains a tyrosine residue, and donate a phosphate group to the tyrosine residue. The intracellular EGFR carrying a phosphorylated tyrosine becomes capable of associating with other intracellular proteins and originates a series of biochemical reactions that propagate downstream through a very complex network. The best known arms of this network are the mitogen-activated protein kinase (MAPK) pathway, which results in tumor cell division upon activation, and the AKT pathway, which results in enhanced cell survival upon activation. The results of EGFR activation are therefore increased cell proliferation and enhanced cellular tolerance to different insults.

Many tumors overexpress EGFR compared to vicinal normal tissues or the epithelial surface from which they originate or have a mutated version of EGFR, intrinsically activated or with an enhanced susceptibility to activation. Such overexpression is thought to be one of the many mechanisms by which tumor cells gain a growth advantage, a key characteristic of the malignant phenotype. Consequently, blocking the EGFR signaling pathway is thought to be a rational strategy for the treatment of many human malignancies. There are basically two ways to inhibit upstream the EGFR signaling pathway: 1) preventing EGF and other natural peptide ligands from binding to the extracellular EGFR domain by the use of specific monoclonal antibodies, and 2) preventing ATP and other phosphate donors from entering the TK pocket of the intracellular EGFR domain by the use of small molecules that structurally fit very well into the pocket (the so-called EGFR TK inhibitors).

After years of discovery efforts and clinical evaluation, EGFR inhibitors have been recently shown to be active antitumor agents against a variety of solid tumors including but not limited to colorectal carcinoma, non-small cell lung cancer, head and neck cancer and malignant gliomas (Conen et al., 2003; Lage et al., 2003; Lorusso, 2003; Vanhoefer et al., 2004). Clinical benefit defined as relief of symptoms or prolongation of survival has been so far demonstrated with the anti-EGFR antibody cetuximab (Erbitux®) and the EGFR tyrosine kinase (TK) inhibitors gefitinib (Iressa®) and erlotinib (Tarceva®). Many additional agents belonging to this class are being developed. As of today, FDA approved indications include chemorefractory colorectal carcinoma and non-small cell lung cancer, head and neck carcinoma, and pancreatic carcinoma. Many clinical studies using these agents alone or in combination, for refractory or chemo naive patients with a variety of other malignant diseases are in progress. It is anticipated that as many as 200,000 patients in the USA may receive these agents every year in the near future.

Although these agents do not cause life threatening toxicities, the major side effect is a skin rash that occurs in 60-70% of patients, affects mostly face and trunk, and causes discomfort and unfavorable cosmetic changes in many cases. Main symptoms caused by the skin rash are itching, dryness, and secondary infection. The occurrence and intensity of the rash are clearly dose-related and the median time of occurrence is 10 days after initiation of therapy. About 10% of patients discontinue therapy due to skin toxicity.

Most clinical studies have shown that most patients who develop skin rash as a result of anti-EGFR therapy tend to live longer. It is thought that the occurrence of skin rash requires both effective EGFR inhibition in the skin and a competent immune system that is able to respond to the tissular insult caused by such inhibition with an appropriate inflammatory response. As there is growing evidence that the skin rash is a surrogate indicator of antitumor efficacy and clinical benefit (Cohen et al., 2003), increasing dosing of anti-EGFR agents to cause a skin rash may become a common practice. If that is the case, treatment of the skin rash will also become of increasing importance. As a result, treatment of the skin rash is also becoming of increasing importance. There are no rational, scientifically proven and clinically effective methods available for the treatment of this form of skin rash. Topical or systemic antibiotics, anti-inflammatory agents, retinoids, topical lubricants, and other types of remedies have been tried in an empirical fashion with poor or inconsistent results. As of today there is no established therapy or prevention for this new skin disease, a condition that is expected to affect about 150,000 individuals in the USA every year in the very near future.

Vitamin K has been used for treatment of blood vessel disorders of the skin, cosmetic skin treatment, and skin treatment following laser treatment (U.S. Pat. No. 5,510,391; U.S. Patent Application Publication No. US 2003/0170187; PCT International Publication Nos. WO 97/39746, WO 02/13780, WO 03/101415, WO 2004/019923; Lou et al., 1999; Shah et al., 2002). However, topical administration of vitamin K3 can cause dermatitis (Page et al., 1942) and vesiculation of the skin (Ulbrich, 1961).

SUMMARY OF THE INVENTION

The present invention provides a method for treating a skin rash secondary to an anti-epidermal growth factor receptor (EGFR) therapy in a subject receiving said therapy, the method comprising applying a vitamin K analog to the skin rash in an amount effective to treat the skin rash. The invention also provides a method for preventing a skin rash secondary to an anti-epidermal growth factor receptor (EGFR) therapy in a subject receiving said therapy, the method comprising applying a vitamin K analog to the skin in an amount effective to prevent the skin rash.

The invention provides a pharmaceutical composition comprising an amount of a vitamin K analog effective to treat or prevent a skin rash secondary to an anti-epidermal growth factor receptor (EGFR) therapy.

The invention also provides a method for identifying a compound that may be useful for treating and/or preventing a skin rash secondary to an anti-epidermal growth factor receptor (EGFR) therapy, the method comprising determining whether the compound activates any one of EGFR, Akt, and Signal Transducer and Activator of Transcription-3 (STAT-3), wherein activation of EGFR, Akt or Stat-3 by the compound is indicative that the compound is effective for treating and/or preventing the skin rash.

The present invention is also directed to a method for treating a skin rash secondary to an anti-epidermal growth factor receptor (EGFR) therapy in a subject receiving said therapy, the method comprising applying a phosphatase inhibitor to the skin rash in an amount effective to treat the skin rash. The invention further provides a method for preventing a skin rash secondary to an anti-epidermal growth factor receptor (EGFR) therapy in a subject receiving said therapy, the method comprising applying a phosphatase inhibitor to the skin in an amount effective to prevent the skin rash.

The invention also provides a pharmaceutical composition comprising an amount of a phosphatase inhibitor effective to treat or prevent a skin rash secondary to an anti-epidermal growth factor receptor (EGFR) therapy.

The invention also provides a method for treating a skin or mucosal ulceration in a subject, the method comprising applying to the skin or mucosal ulceration an amount of a vitamin K analog effective to treat the skin or mucosal ulceration, wherein the vitamin K analog activates EGFR. The invention further provides a method for treating a skin or mucosal ulceration in a subject, the method comprising applying to the skin or mucosal ulceration an amount of a phosphatase inhibitor effective to treat the skin or mucosal ulceration, wherein the phosphatase inhibitor inhibits dephosphorylation of EGFR.

BRIEF DESCRIPTION OF THE FIGURES

FIG. 1A-1C. Effects of Vitamins K1, K2 and K3 (VK1, VK2, VK3) on the phosphorylation of EGFR (A), AKT (B) and Stat-3 (C) in human A431 vulvar carcinoma cells. A431 cells ($1\times10^6$ cells/well) were plated in a 6-well plate, and incubated in RPMI-1640 medium with 10% serum overnight. Cells were exposed to the indicated concentrations of VK1, VK2 and VK3 for 2 hours. Following exposure, cells were washed twice with cold phosphate buffered saline (PBS) solution, and lysed with 50 µl of lysis buffer. Equal amounts of lysate (30 µg of protein) were subjected to a 7.5% or a 12% SDS-PAGE. EGFR, phos-EGFR, AKT, phos-AKT, Stat-3, and phos-Stat-3 were detected by immunoblotting analysis using corresponding antibodies. Vitamin K3 stimulated EGFR, Akt and Stat-3. Vitamin K1 also activated EGFR, whereas Vitamin K2 had little or no effect.

FIG. 4A-4B. VK3-induced phosphorylation of EGFR is reversible in A431 cells. Cells were exposed to 0.1 mM VK3 for 1 hour. Following exposure, cells were washed three times with cold medium and then reincubated in VK3-free fresh medium with 10% fetal bovine serum for the indicated times. Cells were harvested and lysed with lysis buffer. Equal amounts of cell lysate were subjected on 7.5% SDS-PAGE (A). The total EGFR and phosphorylated EGFR (p-EGFR) were detected by immunoblot analysis using corresponding antibodies. Control (Con) means cells were not exposed to VK3. The relative p-EGFR was expressed as the intensity of p-EGFR bands in each time points measured by a laser densitometry compared with that in control as one (B).

FIG. 5. Vitamin K3 inhibits phosphatase activity. A431 cells were exposed to 0.1 mM VK3 for 1 hour. After exposure, cells were washed three times with cold medium and then reincubated in VK3-free medium with 10% fetal bovine serum for the indicated time. Cells were harvested and cell extracts were prepared for the assay of phosphatase activity using pNPP (4-nitrophenyl phosphate disodium) as a substrate. Control (Con) means the phosphatase activity in cells without exposure to VK3. The relative phosphatase activity was expressed as compared with that in control as one. VK3-induced phosphatase inhibition is reversible following removal of VK3.

DETAILED DESCRIPTION OF THE INVENTION

The present invention is directed to a method for treating a skin rash secondary to an anti-epidermal growth factor receptor (EGFR) therapy in a subject receiving said therapy, the method comprising applying a vitamin K analog to the skin rash in an amount effective to treat the skin rash.

As used herein, the term "treat" a skin rash secondary to anti-EGFR therapy means to reduce or eliminate the skin rash, and/or to decrease or eliminate the increase or spread of the skin rash on the subject's skin.

Subjects receiving anti-EGFR therapy include patients receiving treatment with an anti-EGFR antibody such as cetuximab and/or with an EGFR tyrosine kinase inhibitor such as gefitinib or erlotinib.

As used herein, a "vitamin K analog" is a compound selected from the group consisting of vitamin K1 (2-methyl-3-phytyl-1,4-naphthoquinone), vitamin K2 (2-methyl-3-hexaprenyl-1,4-naphthoquinone; menaquinone), vitamin K3 (2-methyl-1,4-naphthoquinone; menadione), vitamin K4 (1,4-diacetoxy-2-methylnaphthalene), vitamin K5 (4-amino-2-methyl-1-naphthalenol), vitamin K6, vitamin K7 (3-methyl-4-amino-1-naphthol hydrochloride), menadione diphosphate, menadione sodium bisulfite, and compounds having the structure:

where R=H or a saturated or unsaturated aliphatic hydrocarbon; and $R_1$ and $R_2$=H or $CH_3$.

Vitamin K3 and vitamin K1 are preferred vitamin K analogs. Vitamin K3 is most preferred. Vitamin K3 has the structure:

Vitamin K1 has the structure:

Preferred forms of vitamin K1 are the trans isomer of vitamin K1 or an admixture of the trans and cis isomers, since the cis isomer has little or no biological activity (Matschiner et al., 1972).

Vitamins K1 and K2 occur naturally. Vitamins K3, K4, K5, K6, and K7 are synthetic analogs. Processes have been described for preparing vitamin K analogs, e.g., U.S. Pat. Nos. 4,374,775, 4,906,411, 5,412,124, 5,637,741, 5,770,774, and 6,579,994, and Sah (1949-50). Vitamins K1, K2 and K3 are available, e.g., from Sigma-Aldrich.

The vitamin K analog can activate EGFR, Akt and/or Stat-3. Vitamin K analogs can be screened to identify those that activate EGFR, Akt and/or Stat-3 using procedures described in the present application. As used herein, to "activate" EGFR, Akt and/or Stat-3 means to increase the phosphorylated form of EGFR, Akt and/or Stat-3.

As used herein to treat a skin rash, the vitamin K analog is topically applied to the skin. Vitamin K compounds are easily soluble in ethyl alcohol and organic solvents and can be prepared in formulations for topical use at desired concentrations. The vitamin K analog may be applied to the skin using, e.g., creams, gels, emulsions, lotions, liquids and/or liposomes. The formulation can be a formulation that provides sustained-release of the vitamin K analog. Topical skin formulations can include, for example, ingredients which include but are not limited to any of the following: ethyl alcohol, isopropyl alcohol, benzyl alcohol, cetyl alcohol, stearyl alcohol, lecithin granules, isopropyl palmitate, isopropyl myristinate, propyl paraben, methyl paraben, a surfactant (e.g., Pluronic F-127 NF), Dowicil 200, mineral oil, natural oil, silicone oil, paraffin, glycerine, stearic acid diester, glycerol stearate, stablizers such as cyclodextrin, and ultraviolet (UV) filters.

Vitamin K analogs can be applied to the skin up to the maximum tolerated dose, which may vary from subject to subject and depend upon the specific vitamin K analog used in treatment. The maximum tolerated dose can be readily determined by one skilled in the art. Preferably, the vitamin K analog is applied to the skin at a concentration of at least 100 μM or at least 15 μg/ml. Preferably, vitamin K3 is applied at a concentration of 50 μg/ml to 200 μg/ml, more preferably 75 μg/ml to 100 μg/ml. Preferably, vitamin K1 is applied to the skin at a concentration of at least 450 μg/ml.

Treatment with the vitamin K analog can start, for example, on the day of initiation of therapy with an anti-EGFR agent or as soon as a skin rash appears or as otherwise prescribed by a physician. The vitamin K analog is administered periodically during the course of therapy with the anti-EGFR agent. The frequency of administration will vary according to the formulation, for example twice a day, daily or every other day or as otherwise prescribed by a physician. A sustained release formulation will require less frequent administration than a formulation that does not provide sustained or slow release of the vitamin K analog.

The invention further provides a method for preventing a skin rash secondary to an anti-epidermal growth factor receptor (EGFR) therapy in a subject receiving said therapy, the method comprising applying a vitamin K analog to the skin in an amount effective to prevent the skin rash, as described herein for treatment of a skin rash. Skin rash secondary to anti-EGFR therapy commonly occurs on the face and trunk. Preferably, the vitamin K analog is applied to areas of the body where the skin rash typically appears secondary to anti-EGFR therapy, such as the face and trunk, or to an area of the body where the subject has experienced a skin rash during prior anti-EGFR therapy. In order to prevent the skin rash, the vitamin K analog can be applied to the skin starting, for example, on the day of initiation of therapy with the anti-EGFR agent or as otherwise prescribed by a physician.

The invention also provides a pharmaceutical composition comprising an amount of any of the vitamin K analogs described herein effective to treat and/or prevent a skin rash secondary to an anti-epidermal growth factor receptor (EGFR) therapy. The compositions can also include a pharmaceutically acceptable carrier. As used herein, the term "carrier" encompasses standard pharmaceutical carriers such as ethyl alcohol and organic solvents. In a preferred embodiment, the pharmaceutical composition is formulated for topical administration. The vitamin K analog can be formulated in a sustained release formulation.

The invention also provides methods for identifying a compound that may be useful for treating and/or preventing a skin rash secondary to an anti-epidermal growth factor receptor (EGFR) therapy, where the method comprises determining whether the compound activates any one or more of EGFR, Akt, and Signal Transducer and Activator of Transcription-3 (STAT-3), wherein activation of EGFR, Akt or Stat-3 by the compound is indicative that the compound is effective for treating and/or preventing the skin rash. Activation of EGFR, Akt or Stat-3 can be determined, e.g., by using an antibody that is specific for the phosphorylated (activated) form of EGFR, Akt or Stat-3. The compound can be, for example, a vitamin K analog. The compound can inhibit dephosphorylation of EGFR, Akt or Stat-3. The compound can be a phosphatase inhibitor.

The present invention is also directed to a method for treating a skin rash secondary to an anti-epidermal growth factor receptor (EGFR) therapy in a subject receiving said therapy, the method comprising applying a phosphatase inhibitor to the skin rash in an amount effective to treat the skin rash. The invention further provides a method for preventing a skin rash secondary to an anti-epidermal growth factor receptor (EGFR) therapy in a subject receiving said therapy, the method comprising applying a phosphatase inhibitor to the skin in an amount effective to prevent the skin rash. Preferably, the phosphatase inhibitor inhibits dephosphorylation of EGFR. A variety of phosphatase inhibitors have been described (for example, Bae et al. 2004, Gerling et al. 2004, Lee and Burke 2003, Liem et al. 2004, U.S. Pat. Nos. 5,155,031 and 6,428,949 B1, U.S. Patent Application Publication No. US 2004/0138218 A1). The phosphatase inhibitor may be applied to the skin using, e.g., creams, gels, emulsions, lotions, liquids and/or liposomes. The formulation can be a formulation that provides sustained-release of the phosphatase inhibitor. The phosphatase inhibitor can be applied to the skin up to the maximum tolerated dose, which may vary from subject to subject and depend upon the specific phosphatase inhibitor used in treatment. The maximum tolerated dose can be readily determined by one skilled in the art.

The invention also provides a pharmaceutical composition comprising an amount of a phosphatase inhibitor effective to treat or prevent a skin rash secondary to an anti-epidermal growth factor receptor (EGFR) therapy. Preferably, the phosphatase inhibitor inhibits dephosphorylation of EGFR. Preferably, the pharmaceutical composition is formulated for topical administration. The phosphatase inhibitor can be formulated in a sustained release formulation.

The invention also provides a method for treating a skin or mucosal ulceration in a subject, the method comprising applying to the skin or mucosal ulceration an amount of a vitamin K analog effective to treat the skin or mucosal ulceration, wherein the vitamin K analog activates EGFR. The invention further provides a method for treating a skin or mucosal ulceration in a subject, the method comprising applying to the skin or mucosal ulceration an amount of a phosphatase inhibitor effective to treat the skin or mucosal ulceration, wherein the phosphatase inhibitor inhibits dephosphorylation of EGFR. Skin and mucosal ulcerative conditions include, for example, ulcerative colitis and oral mucosistis, which can be induced by chemotherapy and/or radiotherapy. For ulcerative colitis, the vitamin K analog or the phosphatase inhibitor can be administered for example by enema administration. Local therapies by enema with steroids and other antiinflammatory agents are currently standard of care for ulcerative colitis. For oral mucosistis, e.g., an adhesive gel or mouth wash containing the vitamin K analog or the phosphatase inhibitor can be used.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Two human cell lines that overexpress non-mutated EGFR were used: A431 vulvar carcinoma and HN5 head and neck carcinoma. Cells were exposed to different concentrations of different vitamin K analogs in the presence of one of three EGFR inhibitors: the anti-EGFR monoclonal antibody cetuximab (Erbitux®) and the EGFR tyrosine kinase inhibitors (TKIs) erlotinib (Tarceva®) and gefitinib (Iressa®). Cytotoxicity was assessed by cell counting. Cells were lysed and the effects of different vitamin K analogs on activation of EGFR, the kinase Akt, and Signal Transducer and Activator of Transcription-3 (STAT-3) were assessed by western blot analysis using antibodies for the phosphorylated (activated) forms of EGFR, Akt and Stat-3. Polyclonal antibodies of anti-EGFR, anti-phos-EGFR (Tyr1068), anti-AKT, anti-phos-AKT (Ser473), anti-Stat-3, and anti-phos-Stat-3 (Tyr-705) were purchased from Cell Signaling (Beverly, Mass.). Vitamins K1, K2, and K3 were purchased from Sigma-Aldrich (St Louis, Mo.). Activation of EGFR, Akt and Stat-3 were assessed in the presence and absence of anti-EGFR treatments of the cells. Activation of EGFR by vitamin K analog was also assessed using mouse skin, which was homogenized and lysed after treatment with the vitamin K analog. Phosphatase activity was determined using pNPP (4-nitrophenyl phosphate disodium) as a substrate.

Results

Figures 1A, 1C:
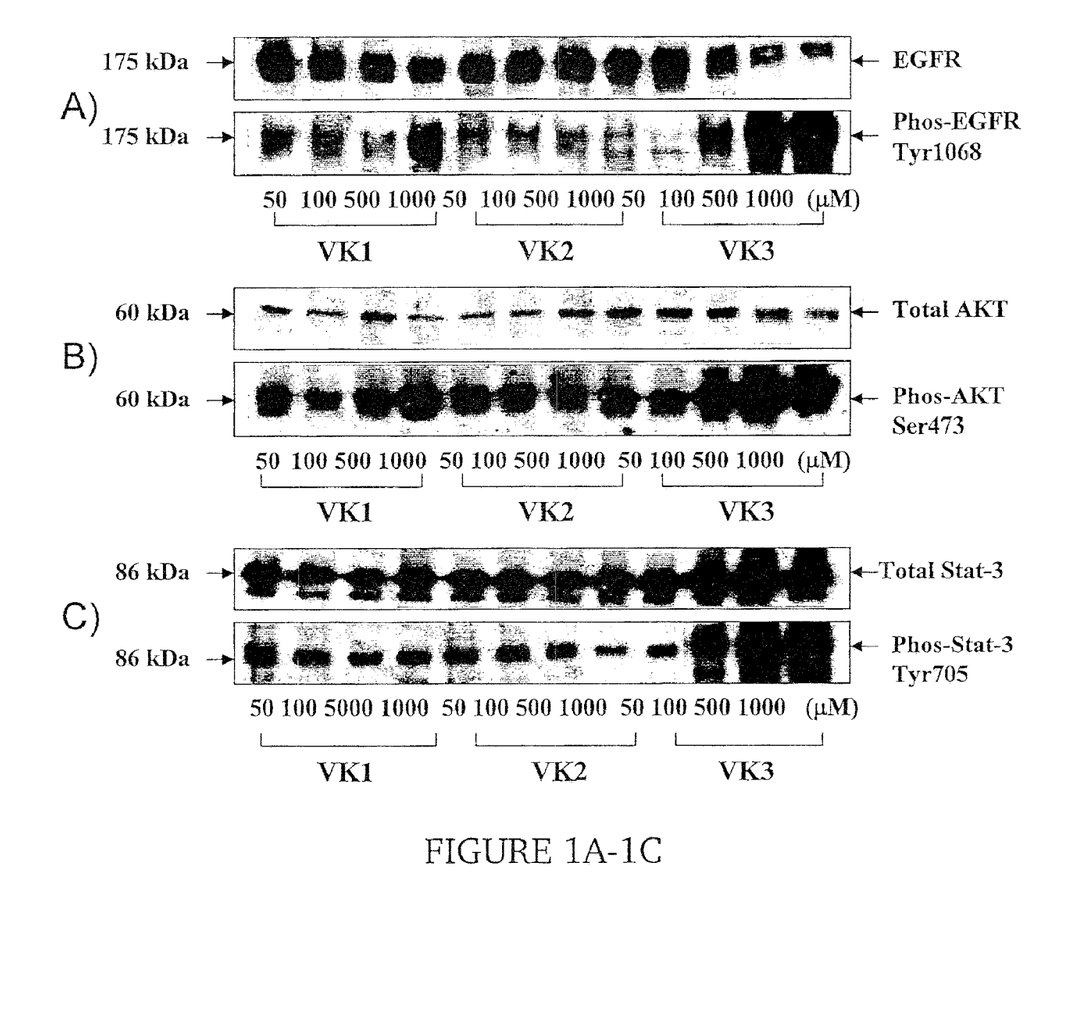

The effects of Vitamins K1, K2 and K3 on activating (phosphorylating) EGFR, Akt and Stat-3 obtained from lysed A431 cells are shown in FIG. 1A-1C. Vitamin K3 activated EGFR and downstream intracellular signaling components Akt and Stat-3. Effects were clearly seen at a Vitamin K3 concentration of 100 μM, or about 17 μg/ml. Vitamin K1 was only effective for activating EGFR and Akt at the highest concentration used (1000 μM or about 450 μg/ml). Vitamin K2 had little or no effect at the concentrations used (up to 1000 μM). Thus, Vitamin K3 is a much more potent stimulant of EGFR, Art and Stat-3 than Vitamin K1 or Vitamin K2. Application of Vitamin K3 to normal mouse skin also activated EGFR.

Figure 6:
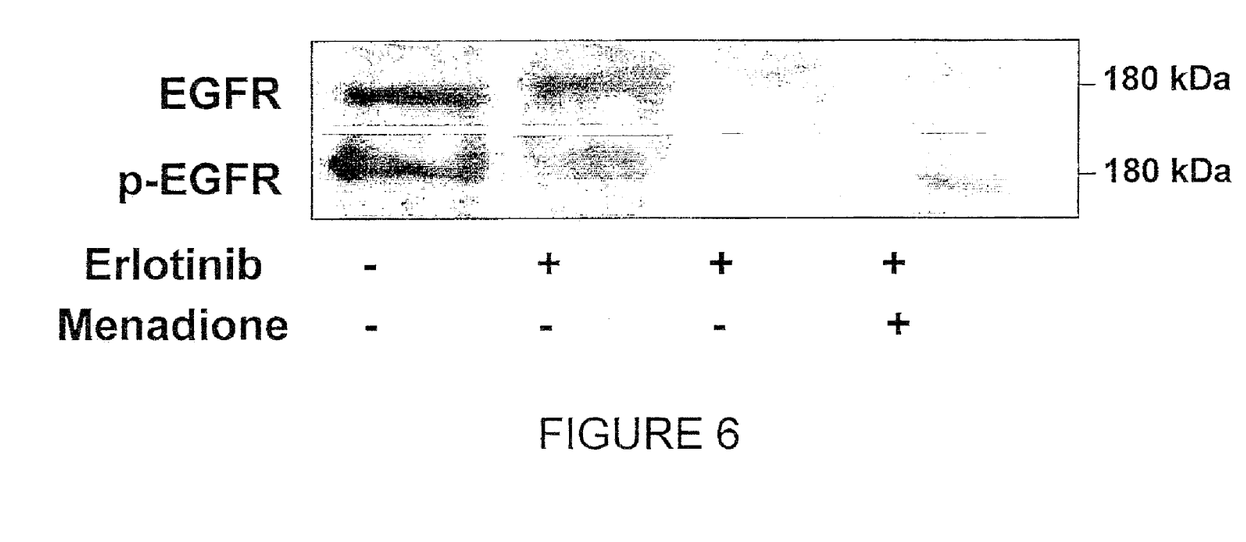
FIG. 6. Effect of Vitamin K3 (menadione) on erlotinib-induced inhibition of EGFR phosphorylation in mouse skin. Vitamin K3 rescues erlotinib-induced inhibition of EGFR phosphorylation in mouse skin tissue. Mice were administrated P.O. daily 50 mg/kg of erlotinib; mouse skin was smeared with VK3 15 mM ethanol solution. After treatment, the mice were sacrificed and skin tissue was taken. 100 mg skin tissue was used for the preparation of tissue extracts. Equal amounts of skin tissue extracts (80 µg of protein) were subjected on a 7.5% SDS-PAGE. Total EGFR and p-EGFR were detected by immunoblot analysis.

Vitamin K3 activation of EGFR, Stat-3 and Akt was tested in the presence of anti-EGFR treatments. A431 cells or HN5 cells stored in serum free medium were treated with the EGFR tyrosine kinase inhibitor erlotinib (2 μM) and with Vitamin K3 (0.01-0.5 mM). Vitamin K3 activated EGFR (FIG. 2) and Stat-3 (at concentrations of 0.1 and 0.5 mM vitamin K3), and Akt (at a concentration of 0.5 mM vitamin K3) in the presence of erlotinib. Similarly, Vitamin K3 (0.1 and 0.5 mM) also activated EGFR, Stat-3 and Akt in the presence of the anti-EGFR monoclonal antibody cetuximab. Vitamin K3 also rescues erlotinib-induced inhibition of EGFR phosphorylation in mouse skin tissue, as shown in FIG. 6.

Figure 2:
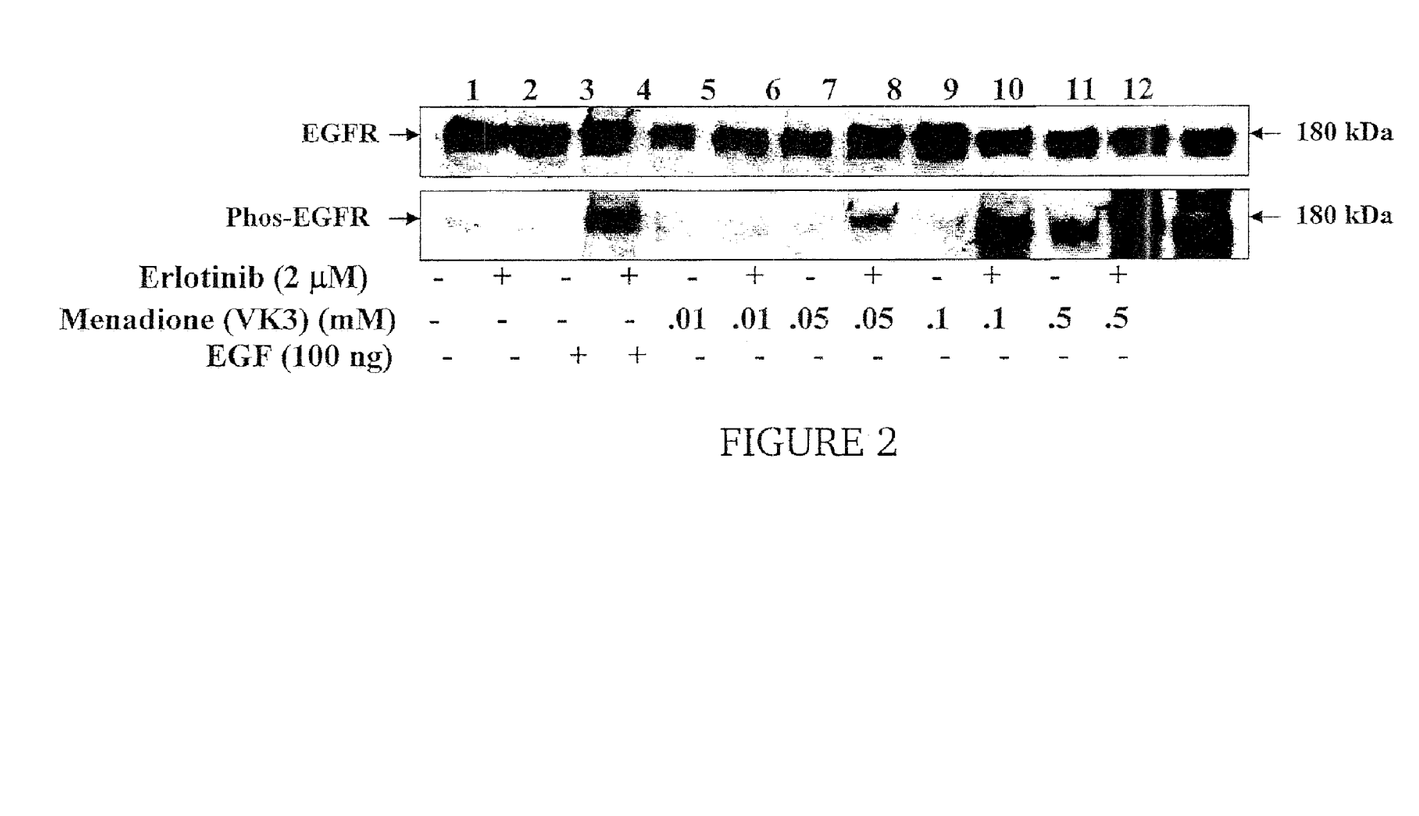
FIG. 2. Vitamin K3 (menadione) prevents the inhibition of EGFR phosphorylation caused by erlotinib, an EGFR tyrosine kinase inhibitor, in A431 cells. A431 cells ($1\times10^6$ cells/well) were plated in a 6-well plate and incubated in RPMI-1640 medium without fetal bovine serum for 24 hours. After starving, cells were exposed to different concentrations of vitamin K3 alone (0.01-0.5 mM) or with 2 µM erlotinib for 2 hours, or stimulated with 100 ng/ml of EGF for 5 min. After exposure, cells were washed twice with cold PBS solution, and lysed with 50 µl of lysis buffer. Equal amounts of lyaste (30 µg of protein) were subjected to a 7.5% SDS-PAGE. EGFR and phosphorylated EGFR were detected by immunoblotting analysis using corresponding antibodies.

Cells were treated with excess EGF to determine if EGF could prevent EGFR inhibition by different anti-EGFR treatments. EGF was effective in preventing EGFR inhibition by the anti-EGFR monoclonal antibody cetuximab, which acts at the extracellular portion of the EGFR. In contrast, treatment of cells with EGF (2 µg/ml) does not prevent EGFR inhibition by the EGFR tyrosine kinase inhibitor erlotinib, which acts at the intracellular portion of the EGFR (FIG. 2).

Figure 3:
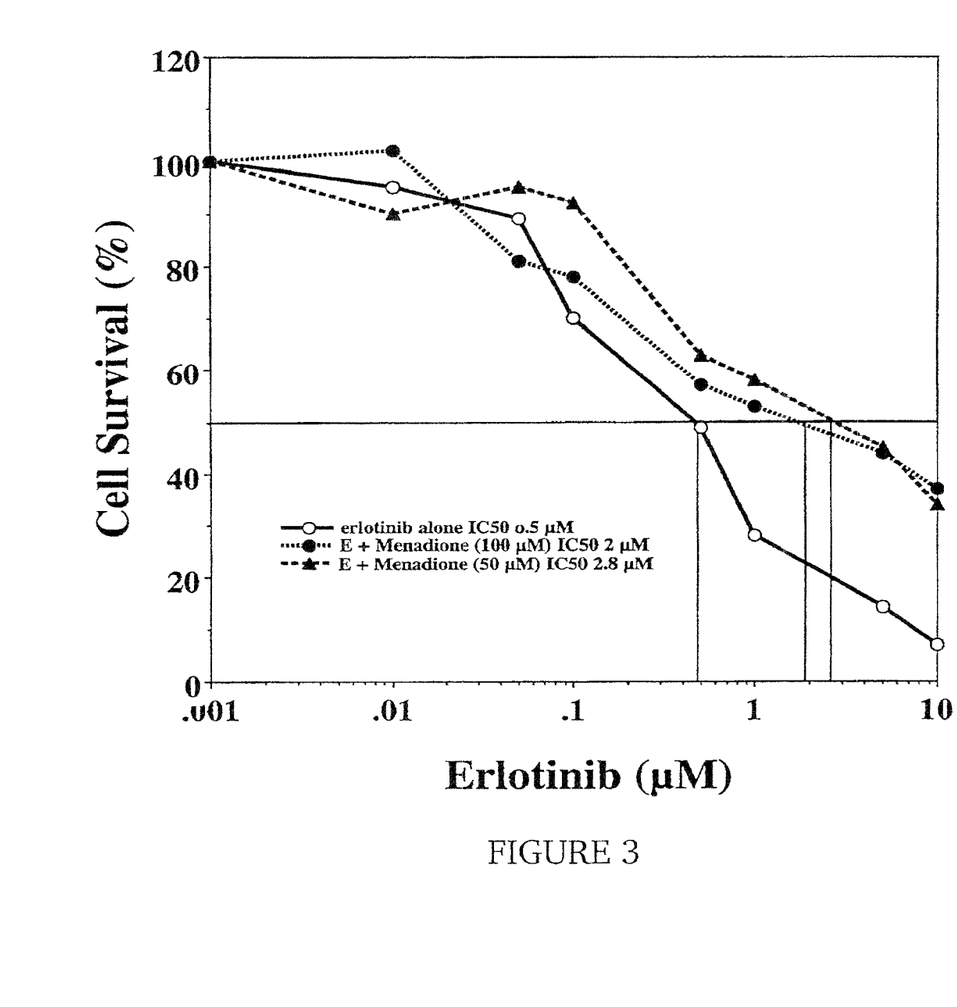
FIG. 3. Effect of VK3 (menadione) on erlotinib-induced cell growth inhibition in A431 cells. Cells were plated in a 96-well plate overnight. Cells were exposed to different concentrations of erlotinib alone or in combination with 50 µM or 100 µM VK3 (menadione) for 72 hours. After exposure, cells were harvested by trypsinization, and the cell viability was assessed by cell counting using a hemacytometer. Each point represents the mean of two independent experiments.
Figures 4A, 4B:
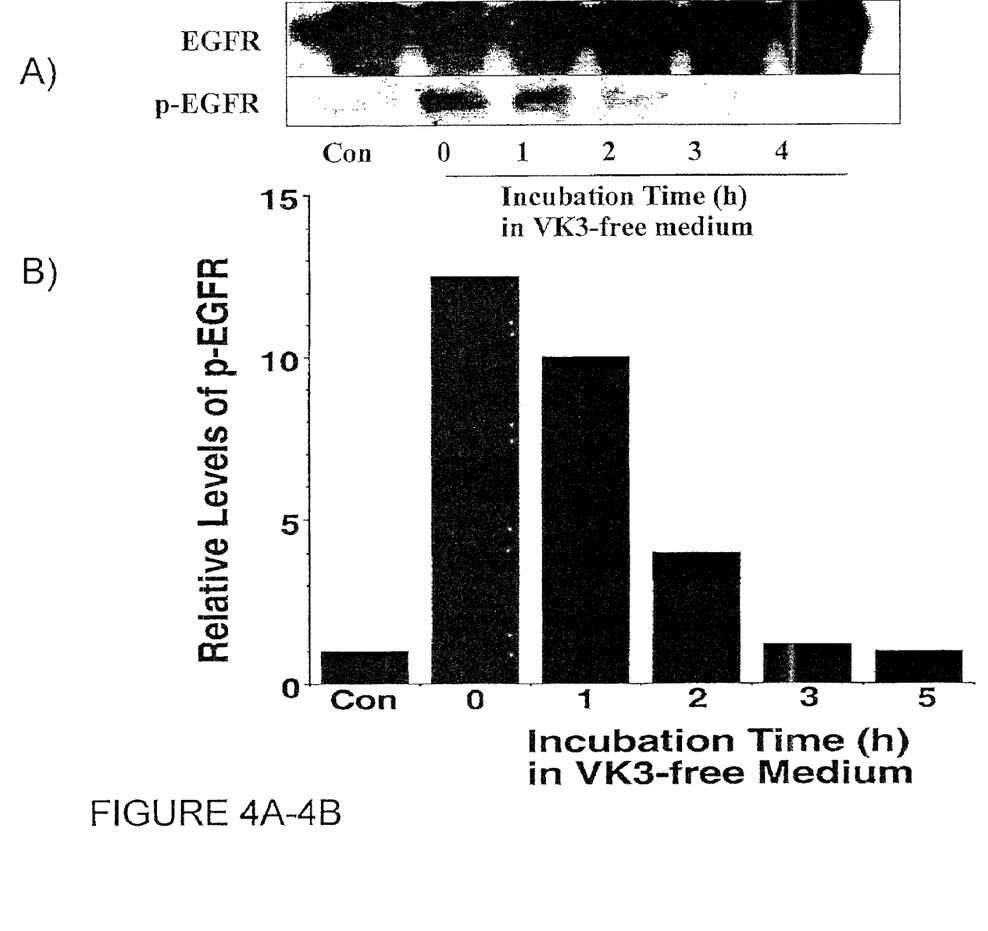

Exposure of human A431 vulvar carcinoma cells to the EGFR tyrosine kinase inhibitor erlotinib results in cell death. Co-incubation of the cells with Vitamin K3 (50-100 µM) decreased the cytotoxicity of the EGFR inhibitor by 4-6 fold. FIG. 3 illustrates results obtained with two different concentrations of Vitamin K3 in rescuing cells treated with erlotinib. The effects of vitamin K3 are reversible. FIG. 4A-4B shows that vitamin K3 induced phosphorylation of EGFR is reversible in A431 cells.

Figure 5:
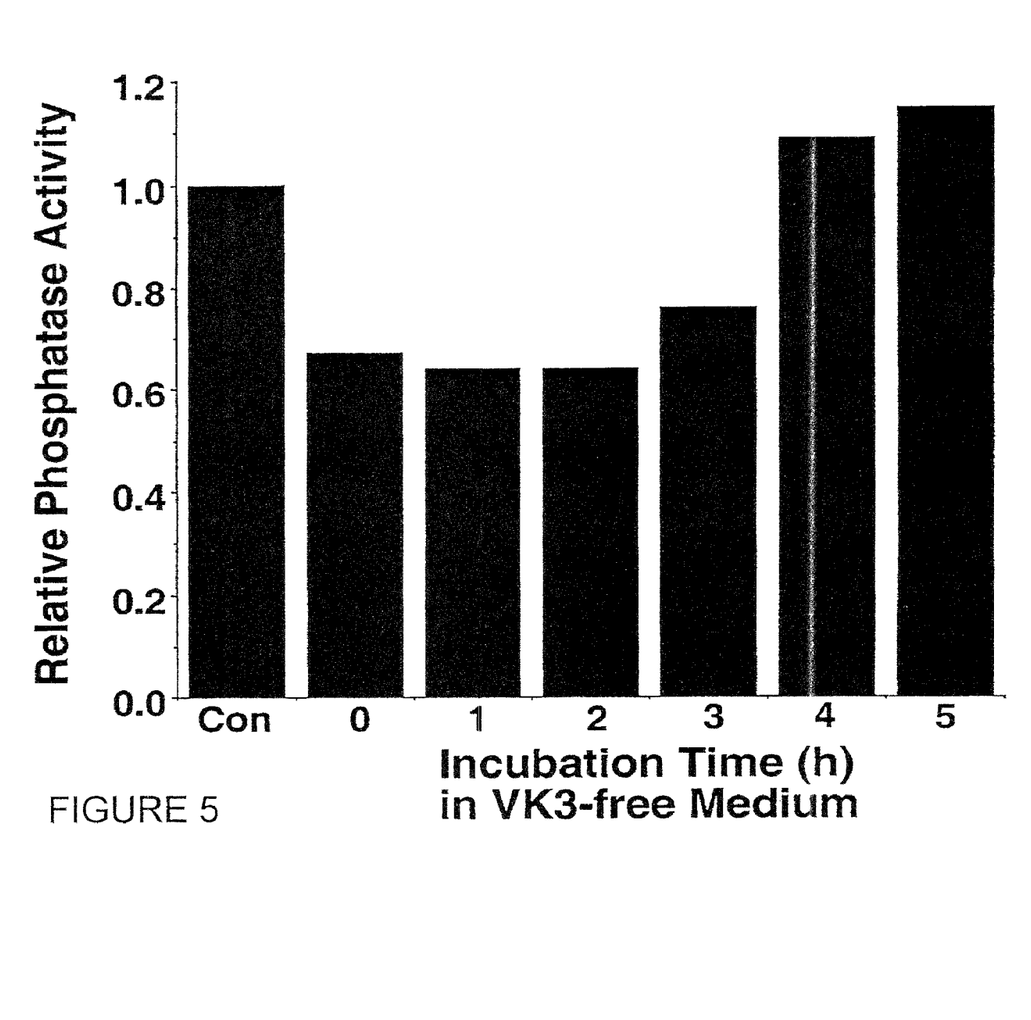

Vitamin K3 acts at least in part by inhibiting phosphatase activity, as shown in FIG. 5. The effect is reversible 2-3 hours after removal of Vitamin K3.

Figure 7:
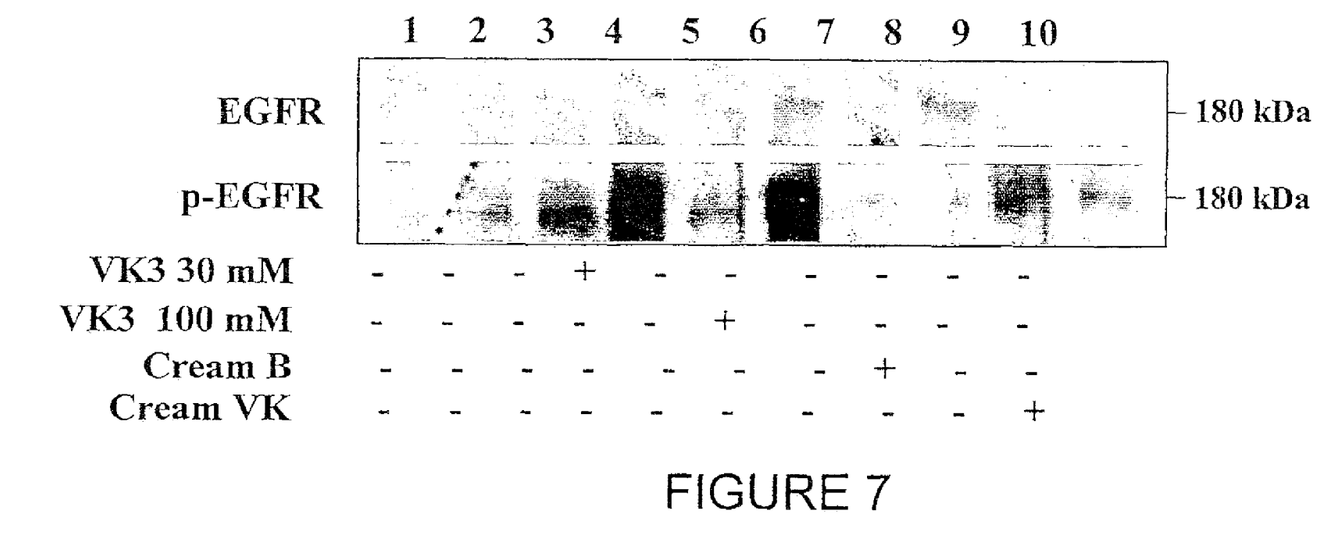
FIG. 7. Effect of VK3, Cream B and Cream VK on EGFR phosphorylation in mouse skin tissue. The mice were smeared with 30 mM or 100 mM VK3 (in ethanol), or with the same doses of Cream B or Cream VK. Following treatment, mice were sacrificed and skin tissues were taken for the preparation of tissue extracts. Equal amounts of tissue extracts (80 µg of protein) were subjected on a 7.5% of SDS-PAGE. Total EGFR and p-EGFR were detected by immunoblot analysis using polyclonal anti-EGFR and p-EGFR antibodies. Cream B is an over the counter product (Baby Cakes) containing Vitamin K3 according to its label; the concentration is not specified. Cream VK is a 5% Vitamin K cream available over the counter. In contrast to 30 mM or 100 mM VK3, the commercial creams do not show an effect.

The effect of Vitamin K3 was examined in the skin of animals receiving the EGFR TK inhibitor erlotinib 100 mg/kg×10 days (days 1-10). Compared to control skin in mice not receiving erlotinib, the skin treated with Vitamin K3 in animals receiving erlotinib showed significant p-EGFR expression, whereas the skin not treated with Vitamin K3 in the same animals showed downregulation of p-EGFR. (FIG. 6). The skin of mice was smeared with Vitamin K3 in ethanol (15 mM BID×5 days on days 5 to 10). The effect of Vitamin K3 was compared to that of two over-the-counter skin creams. Cream B (Baby Cakes) is an over-the-counter product containing Vitamin K3 according to its label; the concentration is not specified. Cream VK is a 5% Vitamin K cream available over-the-counter. The effect of VK3, Cream B and Cream VK on EGFR phosphorylation in mouse skin tissue is shown in FIG. 7. The mice were smeared with Vitamin K3 (in ethanol) 30 mM or 100 mM×3 doses every 12 hours, or with the same doses of Cream B or Cream VK. In contrast to 30 mM or 100 mM VK3, which activates EGFR, the commercial creams do not show an effect.

Discussion

The present application discloses that Vitamin K3 can prevent the EGFR inhibitory effects of anti-EGFR therapy in tumor cell lines of epithelial origin that overexpress EGFR. The EGFR axis in these cells is representative of the EGFR axis in skin keratinocytes. Vitamin K3 had a stimulatory effect on the EGFR intracellular signaling pathway, which was effective even in the presence of anti-EGFR therapy. Vitamin K3 also activated EGFR from normal mammalian (mouse) skin. Weaker stimulatory effects on EGFR were observed with Vitamin K1 but not with Vitamin K2. The present results demonstrate the unexpected effectiveness of Vitamin K3, in comparison to Vitamin K1 or K2 or to two over-the-counter Vitamin K skin creams, in combating anti-EGFR therapy. The use of vitamin K3 for treatment and prevention of a skin rash as disclosed in the present application is counterintuitive in view of previous reports that topical administration of vitamin K3 causes dermatitis (Page et al., 1942) and vesication of the skin (Ulbrich, 1961). Vitamin K3 was also shown to inhibit cellular phosphatase activity, thus providing for the use of phosphatase inhibitors for treatment and prevention of skin rash and related skin or mucosal disorders.

REFERENCES

Bae E Y, Oh H, Oh W K, Kim M S, Kim B S, Kim B Y, Sohn C B, Osada H, Ahn J S. A new VHR dual-specificity protein tyrosine phosphatase inhibitor from Dendrobium moniliforme. Planta Med. 70(9):869-70, 2004.

Cohen E E, Rosen F, Stadler W M, Recant W, Stenson K, Huo D, Vokes E E. Phase II trial of ZD1839 in recurrent or metastatic squamous cell carcinoma of the head and neck. J Clin Oncol. 21(10):1980-7, 2003.

Gerling N, Culmsee C, Klumpp S, Krieglstein J. The tyrosine phosphatase inhibitor orthovanadate mimics NGF-induced neuroprotective signaling in rat hippocampal neurons. Neurochem Int. 2004 June; 44(7):505-20, 2004.

Lage A, Crombet T, Gonzalez G. Targeting epidermal growth factor receptor signaling: early results and future trends in oncology. Ann Med. 35(5):327-36, 2003.

Lee K, Burke T R Jr. CD45 protein-tyrosine phosphatase inhibitor development. Curr Top Med. Chem. 3(7):797-807, 2003.

Liem D A, Gho C C, Gho B C, Kazim S, Manintveld O C, Verdouw P D, Duncker D J. The tyrosine phosphatase inhibitor bis(maltolato)oxovanadium attenuates myocardial reperfusion injury by opening ATP-sensitive potassium channels. J Pharmacol Exp Ther. 2004 June; 309(3): 1256-62. Epub 2004 Mar. 1.

LoRusso P M. Phase I studies of ZD1839 in patients with common solid tumors. Semin Oncol. 30 (1 Suppl 1):21-9, 2003.

Lou W W, Quintana A T, Geronemus R G, Grossman M C. Effects of topical vitamin K and retinol on laser-induced purpura on nonlesional skin. Dermatol Surg. 25(12):942-4, 1999.

Matschiner J T, Bell R G. Metabolism and vitamin K activity of cis phylloquinone in rats. J. Nutr.102(5):625-629, 1972.

Page, R C and Bercovitz, Z. Dermatitis from topical administration of 2-methyl-1:4-naphthoquinone (synthetic vitamin K analogue). Am. J. Med. Sci. 203: 566-569, 1942.

Sah, P P. Synthesis of 3-methyl-4-amino-1-naphthol hydrochloride (vitamin K7) and related vitamin-K-active compounds. Z Vitam Horm Fermentforsch 3(3-4):324-45, 1949-1950.

Shah N S, Lazarus M C, Bugdodel R, Hsia S L, He J, Duncan R, Baumann L. The effects of topical vitamin K on bruising after laser treatment. J Am Acad Dermatol. 47(2):241-4, 2002.

Ulbrich, A P. Topical application of menadione, a synthetic vitamin K: preliminary report. J. Am. Osteopathic Assoc. 60: 370-374, 1961.

Vanhoefer U, Tewes M, Rojo F, Dirsch O, Schleucher N, Rosen O, Tillner J, Kovar A, Braun A H, Trarbach T, Seeber S, Harstrick A, Baselga J. Phase I study of the humanized antiepidermal growth factor receptor monoclonal antibody EMD72000 in patients with advanced solid tumors that express the epidermal growth factor receptor. J Clin Oncol. 22(1):175-84, 2004.

PCT International Publication No. WO 97/39746, Oct. 30, 1997, Method of and composition for treating disorders of the skin using vitamin K.

PCT International Publication No. WO 02/13780, Feb. 21, 2002, Cosmetic cream.

PCT International Publication No. WO 03/101415, Dec. 11, 2003, Compositing comprising vitamin K.

PCT International Publication No. WO 2004/019923, Mar. 11, 2004, Compositions comprising vitamin K for treating or preventing age-related stiffening of arteries.

U.S. Pat. No. 4,374,775, issued Feb. 22, 1983, Dotz K H, Process for preparing vitamin K.

U.S. Pat. No. 4,906,411, issued Mar. 6, 1990, Shinnaka A et al., Process for producing 2-methyl-1,4-naphthoquinone.

U.S. Pat. No. 5,155,031, issued Oct. 13, 1992, Posner et al., Use of pervanadate as an inhibitor of phosphotyrosine phosphatase.

U.S. Pat. No. 5,412,125, issued May 2, 1995, Hamamura K et al., Preparation process of naphthoquinone derivative and intermediate for the preparation thereof.

U.S. Pat. No. 5,510,391, issued Apr. 23, 1996, Elson M L, Method of treating blood vessel disorders of the skin using vitamin K.

U.S. Pat. No. 5,637,741, issued Jun. 10, 1997, Matsumoto Y et al., Process for producing 2-methyl-1,4-naphthoquinone.

U.S. Pat. No. 5,770,774, issued Jun. 23, 1998, Joo Y J et al., Method for preparing 2-methyl-1,4-naphthoquinone (vitamin K3).

U.S. Pat. No. 6,428,949 B1, issued Aug. 6, 2002, Bandman et al., Human phosphatase inhibitor protein.

U.S. Pat. No. 6,579,994, issued Jun. 17, 2003, Sankarasubbier N et al., Process for preparation of 2-methyl-1,4-naphthoquinone.

U.S. Patent Application Publication No. US 2003/0170187, published Sep. 11, 2003, Marchal A, Skin treatments containing nano-sized vitamin K.

U.S. Patent Application Publication No. US 2004/0138218 A1, published Jul. 15, 2004, Pallen et al., Novel protein tyrosine phosphatase inhibitor.

The invention claimed is:

1. A method for reducing the likelihood of developing a skin rash secondary to an anti-epidermal growth factor (EGFR) therapy in a subject in need of the therapy, the method comprising applying vitamin K3 to the skin of the subject prior to occurrence of the rash in an amount effective to reduce development of the rash.

2. The method of claim 1, wherein the vitamin K3 is applied to the face.

3. The method of claim 1, wherein the anti-EGFR therapy is treatment with an anti-EGFR antibody.

4. The method of claim 3, wherein the anti-EGFR antibody is cetuximab.

5. The method of claim 1, wherein the anti-EGFR therapy is treatment with an EGFR tyrosine kinase inhibitor.

6. The method of claim 5, wherein the EGFR tyrosine kinase inhibitor is gefitinib or erlotinib.

7. The method of claim 1, wherein the vitamin K3 activates EGFR.

8. The method of claim 1, wherein the vitamin K3 is formulated in a pharmaceutical formulation suitable for topical administration.

9. The method of claim 1, wherein the vitamin K3 is applied to the trunk.

10. The method of claim 1, comprising exposing skin cells to at least 0.01 mM vitamin K3.

\* \* \* \* \*